US011000222B2

(12) United States Patent
Chakravarty et al.

(10) Patent No.: US 11,000,222 B2
(45) Date of Patent: May 11, 2021

(54) PARTICLE FILTERING FOR CONTINUOUS TRACKING AND CORRECTION OF BODY JOINT POSITIONS

(71) Applicant: Tata Consultancy Services Limited, Mumbai (IN)

(72) Inventors: Kingshuk Chakravarty, Kolkata (IN); Aniruddha Sinha, Kolkata (IN); Soumya Rajan Tripathy, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 158 days.

(21) Appl. No.: 16/523,491

(22) Filed: Jul. 26, 2019

(65) Prior Publication Data

US 2020/0054276 A1    Feb. 20, 2020

(30) Foreign Application Priority Data

Aug. 29, 2018    (IN) .............................. 201821032408

(51) Int. Cl.
*A61B 5/00*    (2006.01)
*G06T 7/30*    (2017.01)
(Continued)

(52) U.S. Cl.
CPC .......... *A61B 5/4528* (2013.01); *A61B 5/1121* (2013.01); *G06T 7/30* (2017.01);
(Continued)

(58) Field of Classification Search
CPC ........... G06K 9/00375; G06K 9/00335; G06K 9/00369; G06K 9/00342
See application file for complete search history.

(56) References Cited

U.S. PATENT DOCUMENTS 9,383,895 B1    7/2016 Vinayak et al.
2016/0247017 A1    8/2016 Sareen et al.

FOREIGN PATENT DOCUMENTS

JP    2012215555    11/2012

OTHER PUBLICATIONS

Saboune, Jamal, and Francois Charpillet. "Using interval particle filtering for marker less 3D human motion capture." 17th IEEE International Conference on Tools with Artificial Intelligence (ICTAI'05). IEEE, 2005. (Year: 2005).*

(Continued)

*Primary Examiner* — Vincent Rudolph
*Assistant Examiner* — Raphael Schwartz
(74) *Attorney, Agent, or Firm* — Finnegan, Henderson, Farabow, Garrett & Dunner, LLP

(57) ABSTRACT

Skeletal recording devices (e.g., Microsoft Kinect®) has been gaining popularity in home-based rehabilitation solution due to its affordability and ease of use. It is used as a marker less human skeleton tracking device. However, apart from the fact that the skeleton data are contaminated with high frequency noise, the major drawback lies in the inability to retain the anthropometric properties, for example, the body segments' length, which varies with time during the tracking. Embodiments of the present disclosure provide systems that implement a particle filter based approach to track the human skeleton data in presence of high frequency noise and multi-objective genetic technique is further implemented to reduce the bone length variations. Further multiple segments in skeleton are filtered simultaneously and segments' lengths are preserved by considering their interconnection for obtained corrected set of body joint positions which ensures that the body segment length is maintained close to ground truth.

18 Claims, 7 Drawing Sheets

(51) Int. Cl.
| | |
|---|---|
| *A61B 5/11* | (2006.01) |
| *G06T 7/60* | (2017.01) |
| *G06F 3/01* | (2006.01) |
| *G06K 9/00* | (2006.01) |

(52) U.S. Cl.
CPC ............... *G06T 7/60* (2013.01); *G06F 3/011* (2013.01); *G06K 9/00369* (2013.01); *G06T 2207/10028* (2013.01)

(56) References Cited

OTHER PUBLICATIONS

Alcoverro, Marcel, Josep Ramon Casas, and Montse Pardas. "Skeleton and shape adjustment and tracking in multicamera environments." International Conference on Articulated Motion and Deformable Objects. Springer, Berlin, Heidelberg, 2010. (Year: 2010).*

Arulampalam M.S. et al., A tutorial on Particle Filters for Online Nonlinear/Non-Gaussian Bayesian Tracking, IEE Transactions, vol. 50, No. 2, Feb. 2002, pp. 174-188.

Bonnechere B. et al., "What are the Current Limits of the Kinect™ Sensor?" Proc. $9^{th}$ Intl Conf. Disability, Virtual Reality & Associated Technologies, Laval, France, Sep. 10-12, 2012, pp. 287-294.

Malinowski, M.J. et al. (May 2015) "On using the Microsoft Kinect™ sensors to determine the lengths of the arm and leg bones of a human subject in motion," located at https://arxiv.org/abs/1505.00371. (23 pages).

Deb, K. et al., "A Fast and Elitist Multi-Objective Genetic Algorithm: NSGA-II", Indian Institute of Technology Kanpur Kanpur, PIN 208 016, India, KanGAL Report No. 200001, (20 pages).

Heris, S.M.K. et al., "Non-dominated Sorting Genetic Filter", $12^{th}$ Iranian Conference on Intelligent Systems, Higher Education Complex of Bam, Bam, Iran, Feb. 4-6, 2014, (6 pages).

Das, P. et al., "Improvement in Kinect Based Measurements Using Anthropometric Constraints for Rehabilitation", IEEE ICC 2017 Symposium E-Health Track, (6 pages).

Tripathy, S.R. et al., "Constrained Kalman Filter for Improving Kinect Based Measurements", 2017 IEEE International Symposium on Circuits and Systems (ISCAS), (4 pages).

Bonnechere, B et al. (2014), "Validity and Reliability of the Kinect Within Functional Assessment Activities: Comparison With Stranded Stereophotogrammetry", Gait & Posture, 39, (pp. 593-598).

Yang, N. et al., "A study of the Human-Robot Synchronous Control System based on Skeletal Tracking Technology", IEEE, International Conference on Robotics and Biomimetics (ROBIO), Shenzhen, China, Dec. 2013, pp. 2191-2196.

Edwards, M. et al., "Low-Latency Filtering of Kinect Skeleton Data for Video Game Control", IVCNZ '14, Hamilton, New Zealand, Nov. 19-21, 2014, pp. 190-195.

\* cited by examiner

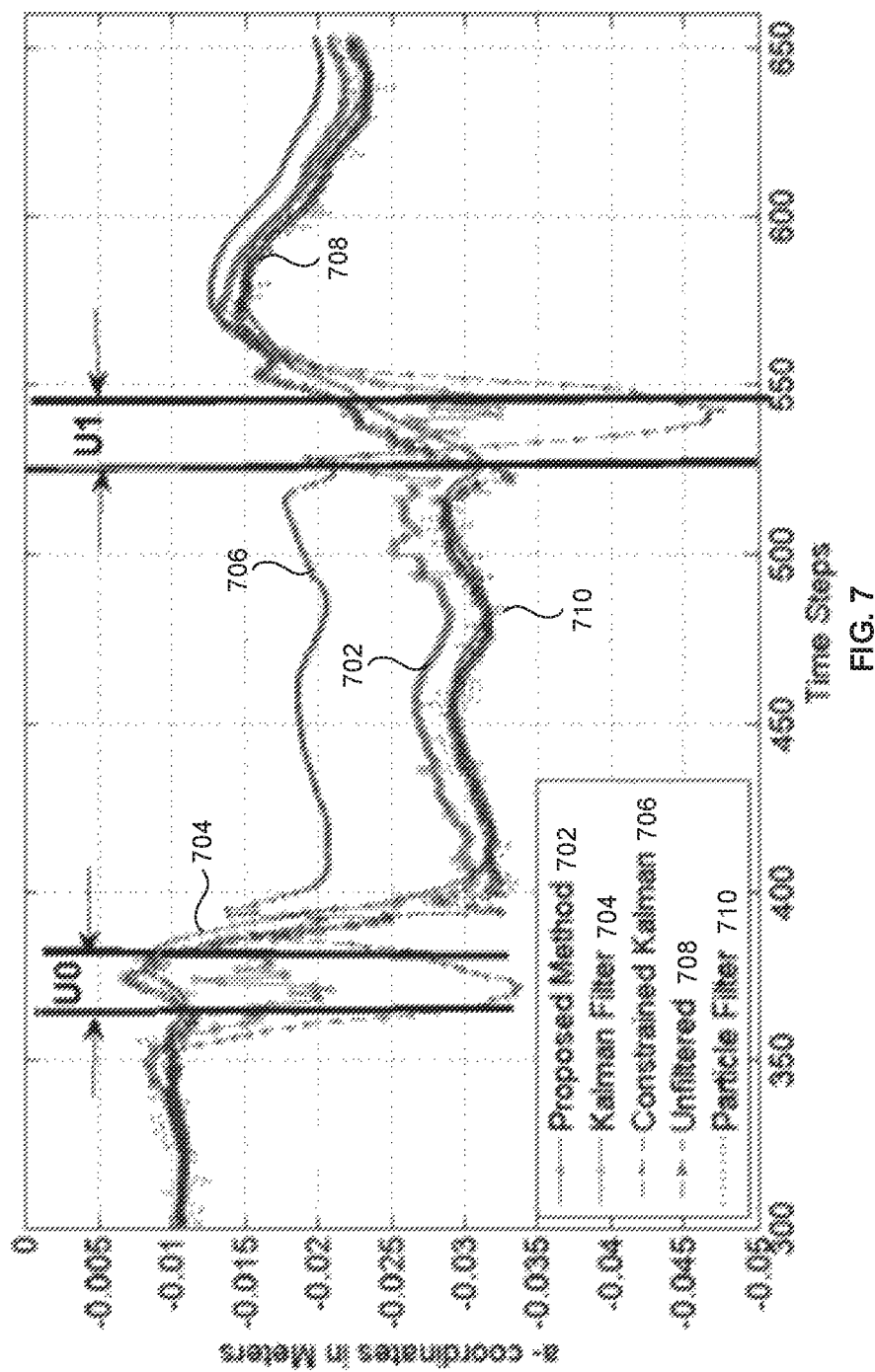

PARTICLE FILTERING FOR CONTINUOUS TRACKING AND CORRECTION OF BODY JOINT POSITIONS

PRIORITY CLAIM

This U.S. patent application claims priority under 35 U.S.C. § 119 to Indian Application No. 201821032408, filed on Aug. 29, 2018. The entire contents of the aforementioned application are incorporated herein by reference.

TECHNICAL FIELD

The disclosure herein generally relates to body joint positions tracking and correction, and, more particularly, to particle filtering for continuous tracking and correction of body joint positions.

BACKGROUND

Skeletal tracking device(s), particularly, Microsoft Kinect®, has been gaining popularity in home-based rehabilitation solution due to its affordability and ease of use. It is used as a marker less human skeleton tracking device. However, apart from the fact that skeleton data are contaminated with high frequency noise, the major drawback of the marker less human skeleton tracking device lies in their inability to retain anthropometric properties, like the body segments' length, which varies with time during the tracking.

Over past few decades, several motion capturing technologies have been explored and applied to human monitoring for health care applications. In recent days, the demand for home based affordable rehabilitation has increased for movement analysis in gait, balance and postural stability. This is mainly to prevent fall and improve movement of body parts of people affected by stroke and elderly population. There are mainly two types of movement analysis namely, marker based and marker less. Marker based systems (e.g., Vicon® system(s)) are very much popular in human movement analysis for their reliability, precision and accuracy. However these systems are very expensive and may require skilled personnel for operation. On the other hand, marker less motion tracking solutions are mostly based on radar and ultrasonic technologies. As an example, a radar based system was proposed for gait monitoring. The applicability of these systems in real world is limited due to the problems like multipath fading and very low range of operation etc. Therefore accurate and efficient tracking of the human skeleton data appears to be still a challenging task in the presence of high frequency noise where bone lengths should remain constant throughout the time irrespective of segment orientation.

SUMMARY

Embodiments of the present disclosure present technological improvements as solutions to one or more of the above-mentioned technical problems recognized by the inventors in conventional systems. For example, in one aspect, there is provided a processor implemented method for performing particle filtering for continuous tracking and correction of body joint positions. The method comprises receiving, in a co-ordinate system, an input data (e.g., say Kinect® data) comprising a plurality of body joint positions pertaining to a subject, each of the plurality of body joint positions comprising a plurality of joint coordinates, wherein the plurality of body joint positions are captured by an infrared sensing device; and denoising for each joint, by using a dynamic filtering based technique, the plurality of body joint positions comprising the plurality of joint coordinates to obtain a corrected set of body joint positions pertaining to the subject, wherein the step of denoising the plurality of body joint positions comprises: computing one or more actual body length segments using a plurality of physically connected joints identified from the plurality of body joint positions; forming a state vector based on the plurality of physically connected joints identified from the plurality of body joint positions; tracking at every time instance 't', using the dynamic filtering based technique, a current position of each of plurality of physically connected joints through an estimation of the formed state vector based on each of the plurality of body joint positions obtained from the input data; generating a plurality of particles associated with the estimation of the formed state vector; updating weight of each of the plurality of particles during transition of each of the plurality of particles from one state to another state; computing a first cost function based on the updated weight associated with each of the plurality of particles to ensure dependencies intact for common joint positions; computing a second cost function based on (i) one or more body length segments derived from the plurality of particles and (ii) the one or more actual body length segments; concurrently optimizing, using an optimizing technique, the first cost function and the second cost function to obtain a ranked list of optimized particles based on the plurality of particles; and adjusting the updated weight associated with each of the plurality of particles based on the ranked list of optimized particles to obtain a final state vector comprising the corrected set of body joint positions pertaining to the subject. In an embodiment, the final state vector comprises weight mean of distribution of the ranked list of optimized particles.

In an embodiment, the optimizing technique is a NSGA technique. In an embodiment, the dynamic filtering technique comprises a Linear Dynamic System (LDS) filtering technique. In an embodiment, the plurality of particles are generated using an importance sampling scheme by defining an Importance Density Function (IDF). In an embodiment, each of the one or more actual body length segments is computed based on Euclidean distance between two physically connected joints identified from the plurality of body joint positions.

In another aspect, there is provided a processor implemented system for performing particle filtering for continuous tracking and correction of body joint positions. The system comprises system a memory storing instructions; one or more communication interfaces; and one or more hardware processors coupled to the memory via the one or more communication interfaces, wherein the one or more hardware processors are configured by the instructions to: receive, in the system, an input data (e.g., say Kinect® data) comprising a plurality of body joint positions pertaining to a subject, each of the plurality of body joint positions comprising a plurality of joint coordinates, wherein the plurality of body joint positions are captured by an infrared sensing device; and denoise for each joint, by using a dynamic filtering based technique, the plurality of body joint positions comprising the plurality of joint coordinates to obtain a corrected set of body joint positions pertaining to the subject, wherein the plurality of body joint positions are denoised by: computing one or more actual body length segments using a plurality of physically connected joints identified from the plurality of body joint positions; forming a state vector based on the plurality of physically connected joints identified from the plurality of body joint positions; tracking at every time instance 't', using the dynamic filtering based technique, a current position of each of the plurality of physically connected joints through an estimation of the formed state vector based on each of the plurality of body joint positions obtained from the input data; generating a plurality of particles associated with the estimation of the formed state vector; updating weight of each of the plurality of particles during transition of each of the plurality of particles from one state to another state; computing a first cost function based on the updated weight associated with each of the plurality of particles; computing a second cost function based on (i) one or more body length segments derived from the plurality of particles and (ii) the one or more actual body length segments; concurrently optimizing, using an optimizing technique, the first cost function and the second cost function to obtain a ranked list of optimized particles based on the plurality of particles; and adjusting the updated weight associated with each of the plurality of particles based on the ranked list of optimized particles to obtain a final state vector comprising the corrected set of body joint positions pertaining to the subject. In an embodiment, the final state vector comprises weight mean of distribution of the ranked list of optimized particles.

In an embodiment, the optimizing technique is a NSGA technique. In an embodiment, the dynamic filtering technique comprises a Linear Dynamic System (LDS) filtering technique. In an embodiment, the plurality of particles are generated using an importance sampling scheme by defining an Importance Density Function (IDF). In an embodiment, each of the one or more actual body length segments is computed based on a Euclidean distance between two physically connected joints identified from the plurality of body joint positions.

In yet another aspect, there are provided one or more non-transitory machine readable information storage mediums comprising one or more instructions which when executed by one or more hardware processors causes performing particle filtering for continuous tracking and correction of body joint positions. The instruction comprises receiving, in a co-ordinate system, an input data comprising a plurality of body joint positions pertaining to a subject, each of the plurality of body joint positions comprising a plurality of joint coordinates, wherein the plurality of body joint positions are captured by an infrared sensing device; and denoising for each joint, by using a dynamic filtering based technique, the plurality of body joint positions comprising the plurality of joint coordinates to obtain corrected set of body joint positions pertaining to the subject, wherein the step of denoising the plurality of body joint positions comprises: computing one or more actual body length segments using a plurality of physically connected joints identified from the plurality of body joint positions; forming a state vector based on the plurality of physically connected joints identified from the plurality of body joint positions; tracking at every time instance 't', using the dynamic filtering based technique, a current position of each of plurality of physically connected joints through an estimation of the formed state vector based on each of the plurality of body joint positions obtained from the input data; generating a plurality of particles associated with the estimation of the formed state vector; updating weight of each of the plurality of particles during transition of each of the plurality of particles from one state to another state; computing a first cost function based on the updated weight associated with each of the plurality of particles to ensure dependencies intact for common joint positions; computing a second cost function based on (i) one or more body length segments derived from the plurality of particles and (ii) the one or more actual body length segments; concurrently optimizing, using an optimizing technique, the first cost function and the second cost function to obtain a ranked list of optimized particles based on the plurality of particles; and adjusting the updated weight associated with each of the plurality of particles based on the ranked list of optimized particles to obtain a final state vector comprising the corrected set of body joint positions pertaining to the subject. In an embodiment, the final state vector comprises weight mean of distribution of the ranked list of optimized particles.

In an embodiment, the optimizing technique is a NSGA technique. In an embodiment, the dynamic filtering technique comprises a Linear Dynamic System (LDS) filtering technique. In an embodiment, the plurality of particles are generated using an importance sampling scheme by defining an Importance Density Function (IDF). In an embodiment, each of the one or more actual body length segments is computed based on a Euclidean distance between two physically connected joints identified from the plurality of body joint positions.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 7 depicts a graphical representation illustrating temporal variation of coordinate "a" for joint number 8 in accordance with an example embodiment of the present disclosure.

DETAILED DESCRIPTION

Figure 1:
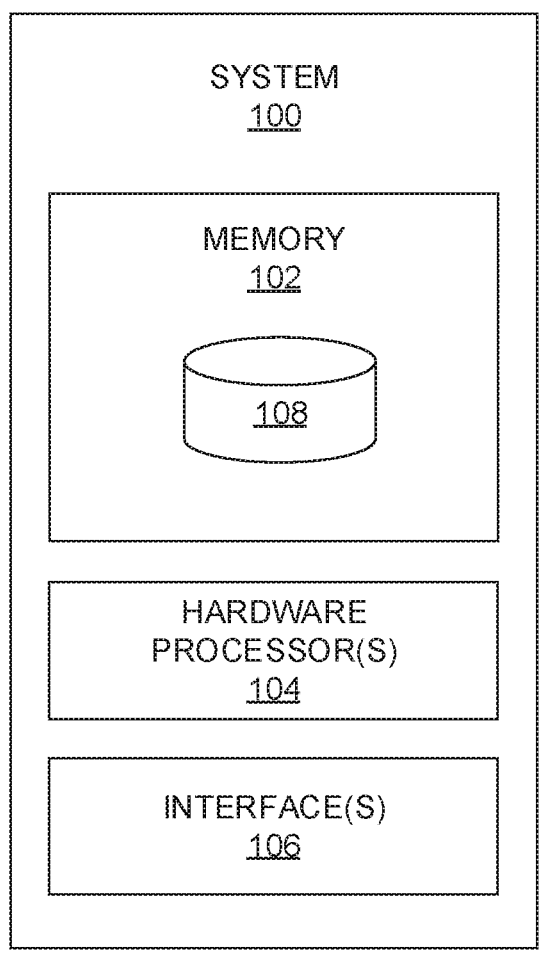
FIG. 1 illustrates an exemplary block diagram of a system for performing particles filtering for continuous tracking and correction of body joint positions of a subject in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Microsoft Kinect® Xbox One is a low cost marker less motion tracking device, which is a potential candidate for 24×7 monitoring device in home rehabilitation solution. It consists of a RGB camera and infrared (IR) based depth sensor, which can track human skeleton joint positions in 3D space similar to other marker based systems (e.g., Vicon systems). The major problem in Kinect® is that the 3D joint positions obtained from Kinect® are noisy which results temporal variation of the body segments' length (bone length) calculated from joint coordinates. Ideally, the bone lengths should remain constant throughout the time irrespective of segment orientation in 3D space irrespective of segment orientation in 3D space or activity being performed. Researches have thoroughly studied variation of eight bone lengths during walking and running in the treadmill. An average bone length disparity of 9-11 cm in Kinect® sensor has been reported (e.g., refer to M. J. Malinowski and E. Matsinos, "On using the Microsoft Kinect™ sensors to determine the lengths of the arm and leg bones of a human subject in motion," ArXiv e-prints, May 2015). Moreover, Kinect® shows significant variation in bone lengths compared to other systems (e.g., Vicon® systems) as discussed in research studies (e.g., see B. Bonnechere, B. Jansen, P. Salvia, H. Bouzahouene, L. Omelina, J. Cornelis, M. Rooze, and S. Van Sint Jan, "What are the current limits of the Kinect® sensor," in Ninth International Conference on Disability, Virtual Reality and Associated Technologies (ICDVRAT), 2012, pp. 287-294). In addition to these discrepancies, Kinect® coordinates are also noisy due to IR interference, external lighting conditions and non-anthropometric skeleton model etc. (e.g., refer to B. Bonnechere, B. Jansen, P. *Salvia*, H. Bouzahouene, L. Omelina, F. Moiseev, V. Sholukha, J. Cornelis, M. Rooze, and S. V. S. Jan, "Validity and reliability of the kinect within functional assessment activities: comparison with standard stereophotogrammetry," Gait & Posture, vol. 39, no. 1, pp. 593-598, 2014). These issues make Kinect® difficult to use in clinical applications, for example, rehabilitation. In order to reduce the noise in joint coordinates, many time domain filters, for example, averaging, median, mean square filters etc. have been proposed (e.g., refer to N. Yang, F. Duan, Y. Wei, C. Liu, J. T. C. Tan, B. Xu, and J. Zhang, "A study of the human-robot synchronous control system based on skeletal tracking technology," in 2013 IEEE International Conference on Robotics and Biomimetics (ROBIO), pp. 2191-2196). Constant Kalman filter and Weiner Process Acceleration (WPA) Kalman filter have been used to smooth and track joint position simultaneously (e.g., refer to M. Edwards and R. Green, "Low-latency filtering of Kinect® skeleton data for video game control," in Proceedings of the 29th International Conference on Image and Vision Computing New Zealand. ACM, 2014, pp. 190-195—hereinafter referred to as 'Edwards et al.'). However, all these methods are mainly inclined on maintaining the latency and improving individual joint positions.

The focus on improving the Kinect® based measurements still appears to be limited. In some research studies, a constrained Kalman filter based method has been proposed to track the joint positions by preserving the bone length over time (e.g., refer to S. R. Tripathy, K. Chakravarty, A. Sinha, D. Chatterjee, and S. K. Saha, "Constrained Kalman filter for improving Kinect® based measurements," in 2017 IEEE International Symposium on Circuits and Systems (ISCAS), pp. 1-4—hereinafter referred to as 'Tripathy et al.'). One of potential drawback of this constrained Kalman filter based method is that it considers a single body segment at a particular time stamp for filtering without considering interconnection between body segments. So naturally filtering of one segment may negatively affect the other connected segments. For example, elbow joint cannot be filtered efficiently by this constrained Kalman filter based method without considering both the arm and forearm simultaneously. While there are other research studies which have taken similar approaches to maintain the bone length constant using a Kalman filter and differential evolution algorithm (e.g., see P. Das, K. Chakravarty, D. Chatterjee, and A. Sinha, "Improvement in Kinect® based measurements using anthropometric constraints for rehabilitation," in 2017 IEEE International Conference on Communications (ICC), pp. 1-6). Such an approach is intended to also suffer from the same problem as that of the constrained Kalman filter based method. Specifically, the constraints formulated in these research studies have focused on preserving the bone length of single body segment at a time without being concerned about structural build of human skeleton.

Embodiments of the present disclosure provide systems and methods that implement particle filtering to preserve the bone lengths of all the connected segments simultaneously by considering their dependencies on each other due to the presence of common joints between them. More specifically, embodiments of the present disclosure and associated systems implement Non-dominated Sorting Genetic Algorithm (NSGA) based particle filtering method such that particle filter can track multiple skeleton joints simultaneously whereas NSGA is responsible for maintaining the bone lengths.

Moreover, objective of the present disclosure also lies in the constraint formulation to ensure that the filtered coordinates do not (drastically) deviate from original coordinates (which ensures smooth tracking). In order to achieve this, the constraint is (mathematically) formulated and applied on both the static and dynamic postures for performance evaluation.

Referring now to the drawings, and more particularly to FIGS. 1 through 7, where similar reference characters denote corresponding features consistently throughout the figures, there are shown preferred embodiments and these embodiments are described in the context of the following exemplary system and/or method.

FIG. 1 illustrates an exemplary block diagram of a system 100 for performing particles filtering for continuous tracking and correction of body joint positions in accordance with an embodiment of the present disclosure. The system 100 may also be referred as 'a body joint positions tracking and detection system' or 'a 3D world co-ordinate system' and interchangeably used hereinafter. In an embodiment, the system 100 includes one or more processors 104, communication interface device(s) or input/output (I/O) interface(s) 106, and one or more data storage devices or memory 102 operatively coupled to the one or more processors 104. The one or more processors 104 may be one or more software processing modules and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the device 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment a database 108 can be stored in the memory 102, wherein the database 108 may comprise, but are not limited to information pertaining to subject (e.g., user). More specifically, information pertaining to the subject may comprise the input data (e.g., Kinect® data) including a plurality of body joint positions that comprise a plurality of joint coordinates. In an embodiment, the memory 102 may store one or more technique(s) (e.g., dynamic filtering technique(s), optimization technique(s) such as Non-dominated Sorting Genetic Algorithm, ranking technique(s), simulation technique(s) such as Monte Carlo (MC) simulations, and the like) which when executed by the one or more hardware processors 104 to perform the methodology described herein. The memory 102 may further comprise information pertaining to input(s)/output(s) of each step performed by the systems and methods of the present disclosure.

Figure 2:
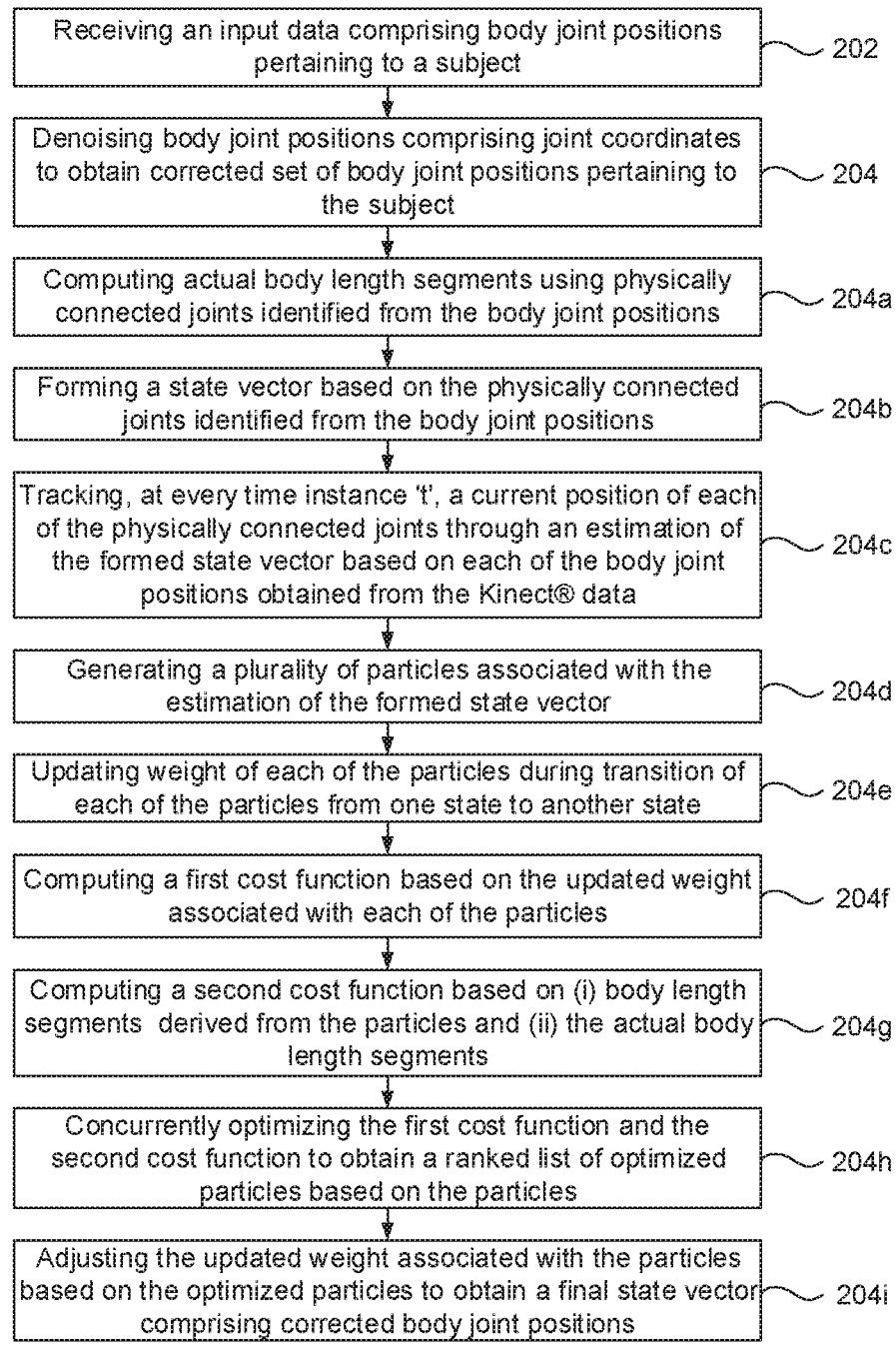
FIG. 2 illustrates an exemplary flow diagram of a method of performing particles filtering for continuous tracking and correction of body joint positions of a subject using the system of FIG. 1 in accordance with an embodiment of the present disclosure.

FIG. 2, with reference to FIG. 1, illustrates an exemplary flow diagram of a method of performing particles filtering for continuous tracking and correction of body joint using the system 100 of FIG. 1 in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 as depicted in FIG. 1, and the flow diagram. In an embodiment of the present disclosure, at step 202, the one or more hardware processors 104 receive, in the system 100, an input data (e.g., say Kinect® data) comprising a plurality of body joint positions pertaining to a subject, each of the plurality of body joint positions comprising a plurality of joint coordinates, wherein the plurality of body joint positions are captured by an Infrared (IR) sensing device (e.g., a Three-Dimensional (3D) motion tracking device, a skeleton recording device, a Kinect® device, and the like). In an embodiment, the input data (e.g., Kinect® data) comprising a plurality of body joint positions (e.g., 3D world coordinates of joint positions) pertaining to a subject may also be referred as Skeletal data and may be interchangeably used herein after. In an embodiment, a body joint position refers to a position at which a body joint (or joint) is present, in one example embodiment. The input data (e.g., Kinect® data) is captured using device(s) such as, IR Projector, IR sensor and RGB camera to track human joint positions in the 3D world co-ordinate system consisting of axes (a, b, c). At any instance of time t the input data (e.g., Kinect® data) provides noisy co-ordinates of N joints (for example, for Kinect® Xbox One/Version 2 N=25), $\chi_t = (a^i, b^i, c^i)$ where i=1, 2, . . . , N. The body segment lengths computed from $\chi_t \forall t=1, 2, \ldots, T$ vary with time, which is quite unexpected in human physical structure. In order to remove this noise, a constraint is formulated based on two factors derived from human physical (skeleton) structure i.e., (i) bones (body segments) are interconnected to each other and (ii) the length between any physically connected joints should remain constant over time. Specifically the constraint is defined in such a way that it tends to preserve the entire human skeleton structure and provide more realistic anthropometric measurements. Hence a dynamic filtering based approach with multiple bone length constraints is proposed to denoise $\chi_t$ obtained from the input data (e.g., Kinect® data). In an embodiment of the present disclosure, at step 204, the one or more hardware processors 104 denoise for each joint, by using a dynamic filtering based technique, the plurality of body joint positions comprising the plurality of joint coordinates. The step of denoising the plurality of body joint positions to obtain corrected body joint positions is described by way of following steps 204a-204i wherein in an embodiment of the present disclosure, at step 204a, the one or more hardware processors 104 compute one or more actual body length segments using a plurality of physically connected joints identified from the plurality of body joint positions. In an embodiment of the present disclosure, each of the one or more actual body length segments is computed based on Euclidean distance between two physically connected joints (or joint positions) identified from the plurality of body joint positions. In the present disclosure, obtaining corrected body joint positions as an output by the system 100 is realized through the fusion of the proposed particle filter technique and Non-dominated Sorting Genetic Algorithm (NSGA). In this context, the bone length constraint is defined:

A pair of joints i and j are said to comply to bone length constraint if the two joints lie on a single bone and their coordinates should follow below equation (1) for all time instances:

$$\|\chi_t^i - \chi_t^j\| = L_{i,j}^2 \tag{1}$$

Where $\chi_t^i$ is the coordinate of $i^{th}$ joint at time t and $L_{i,j}$ is the physical (actual) length of the bone present between those two joints.

Figure 3:
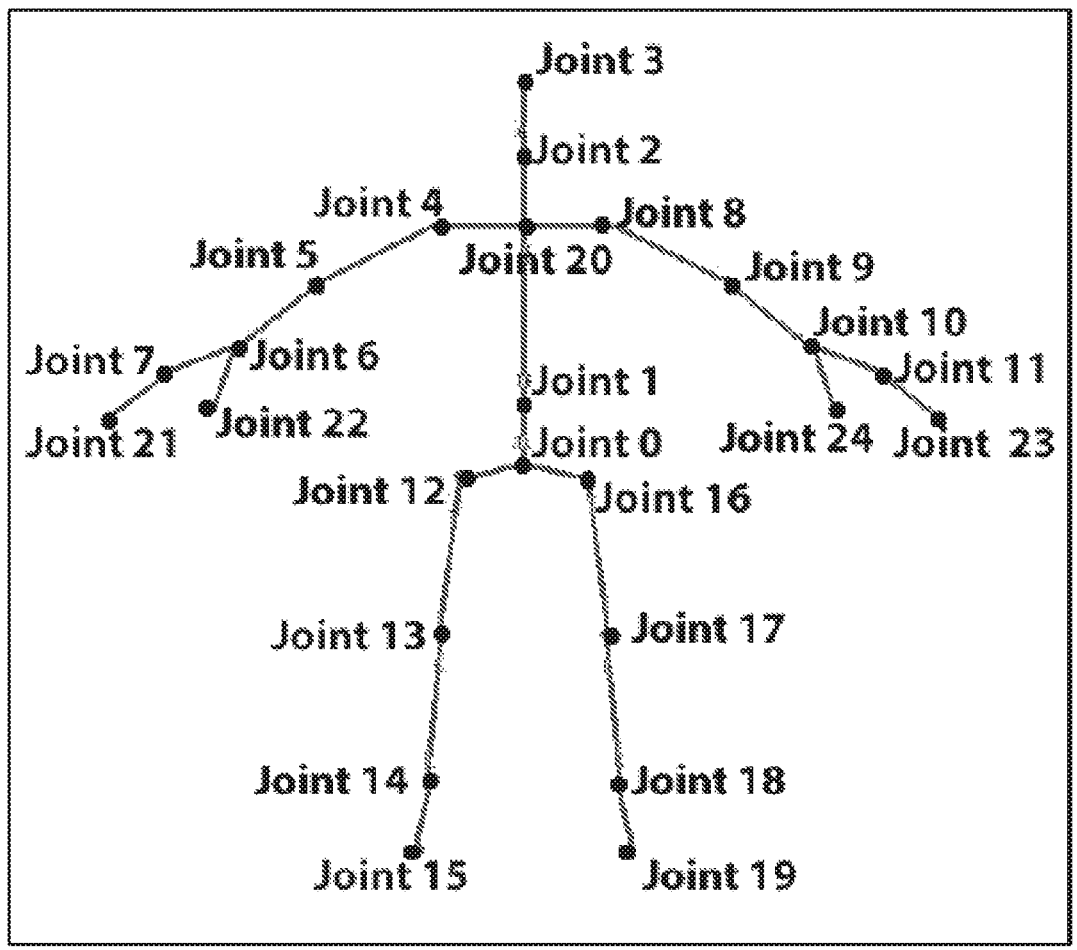
FIG. 3 depicts the plurality of body joint positions obtained from input data (e.g., say Kinect® data) captured using an infrared sensing device in accordance with an embodiment of the present disclosure.

In an embodiment of the present disclosure, at step 204b, the one or more hardware processors 104 form a state vector based on the plurality of physically connected joints identified from the plurality of body joint positions. In other words, in the proposed method, the state vector is formed from $\chi_t$ as $x=[a_1, \ldots, a_m, b_1, \ldots, b_m, c_1, \ldots, c_m]^T$, where m($\leq$N) is the total number of joints considered for filtering. It is to be noted that in the present disclosure and use case scenario, the experiment was performed with only 6 segments and the results have been reported accordingly. However it is to be understood by a person having ordinary skill in the art or person skilled in the art that the proposed method can be extended to all the body segments (which is more than 6) and shall not be construed as limiting the scope of the present disclosure. For instance, in the present disclosure, the state vector contains all the connected body segments, for e.g., 6-5, 5-4, 4-20, 20-8, 8-9, 9-10 are such six segments consisting of seven joints as shown in FIG. 3. More particularly, FIG. 3, with reference to FIGS. 1-2, depicts the plurality of body joint positions obtained from the input data (e.g., Kinect® data) captured using an infrared sensing device in accordance with an embodiment of the present disclosure. In FIG. 3, Joint 0 refers to Spine Base, Joint 1 refers to Spine Mid, Joint 2 refers to Neck, Joint 3 refers to Head, Joint 4 refers to Shoulder Left, Joint 5 refers to Elbow Left, Joint 6 refers to Wrist Left, Joint 7 refers to Hand Left, Joint 8 refers to Shoulder Right, Joint 9 refers to Elbow Right, Joint 10 refers to Wrist Right, Joint 11 refers to Hand Right, Joint 12 refers to Hip Left, Joint 13 refers to Knee Left, Joint 14 refers to Ankle Left, Joint 15 refers to Foot Left, Joint 16 refers to Hip Right, Joint 17 refers to Knee Right, Joint 18 refers to Ankle Right, Joint 19 refers to Foot Right, Joint 20 refers to Spine Shoulder, Joint 21 refers to Hand Tip Left, Joint 22 refers to Thumb Left, Joint 22 refers to Thumb Left, Joint 23 refers to Hand Tip Right and Joint 24 refers to Thumb Right.

Referring back to FIG. 2, In an embodiment of the present disclosure, at step 204c, the one or more hardware processors 104 track, at every time instance 't', using the dynamic filtering based technique, a current position of each of plurality of physically connected joints through an estimation of the formed state vector based on each of the plurality of body joint positions obtained from the input data (e.g., Kinect® data) and a plurality of particles associated with the estimation of the formed state vector are generated at step 204d. In an embodiment of the present disclosure, at step 204e, the one or more hardware processors 104 further update weight of each of the plurality of particles during transition of each of the plurality of particles from one state to another state. In other words, the steps 204c till 204e are better understood by way of example as described below.

The proposed particle filter based method models the joint motion trajectory as a Linear Dynamic Systems (LDS). In this LDS, the states are evolved as $x_t = f(x_{t-1}, u_{t-1})$ where f is a state transition function and $u_t$ is process noise following i.i.d. (independent and identically distributed) $\mathcal{N}(0,\sigma_n)$. The joint position tracking is carried out recursively by estimating $x_t$ at each time step t depending on the Kinect® based measurements $y_t = h(x_t, n_t)$ where h is a measurement function is and $n_t$ is the measurement noise following i.i.d. $\mathcal{N}(0,\sigma_n)$. In the present disclosure, as per the experiment conducted, the covariance matrix of process noise and measurement noise were selected to be diagonal with value 0.01 and this selection shall not be construed as limiting the scope of the present disclosure. The whole process involves two steps called prediction of $x_t$ from measurements $y_{1:t-1}$ and correction of $x_t$ given observed $y_t$ as shown in below equations (2) and (3) respectively:

$$p(x_t | y_{1:t-1}) = \int p(x_t | x_{t-1}) p(x_{t-1} | y_{1:t-1}) dx_{t-1} \quad (2)$$

$$p(x_t | y_{1:t}) = \frac{p(y_t | x_t) p(x_t | y_{1:t-1})}{\int p(y_t | x_t) p(x_t | y_{1:t-1})} \quad (3)$$

The posterior probability density p(.) computed using above equation (3) is approximated with the help of Monte Carlo (MC) simulations. MC simulations approximate the Probability Density Function (PDF) by a set of random samples and corresponding weights as given and expressed in below equation (4):

$$p(x_t|y_{1:t}) = \sum_{i=1}^{S} w_t^i \delta(x_t - x_t^i) \quad (4)$$

Here, S is the number of particles obtained from importance sampling scheme (e.g., refer to M. S. Arulampalam, S. Maskell, N. Gordon, and T. Clapp, "A tutorial on particle filters for online nonlinear/non-gaussian bayesian tracking," IEEE Transactions on signal processing, vol. 50, no. 2, pp. 174-188, 2002—hereinafter referred to as 'Arulampalam et al.') by defining the importance density function q(.), and in the present disclosure and use case scenario value of S=400 and the value of S shall not be construed as limiting the scope of the present disclosure. In other words, the plurality of particles S are generated using an Importance Density Function (IDF), in one example embodiment. The generated S particles undergo state transitions (e.g., from one state to another state as mentioned in step 204e) at each time instance as given in above equation (2) and the corresponding weight with $w_t^i$ of each particle is updated sequentially (e.g., refer to Arulampalam et al.) using below equation (5) expressed by way of example:

$$w_t^j \propto w_{t-1}^j \frac{p(y_t | x_t^j) p(x_t^j | x_{t-1}^j)}{q(x_t^j | x_{t-1}^j, y_t)} \quad (5)$$

The sequential update of equation (5) is simplified (e.g., refer to Arulampalam et al.) to equation (6) by taking $q(x_t^i | x_{t-1}^i, y_t) = p(x_t | x_{t-1}^i)$ wherein equation (6) is now expressed by way of example below:

$$w_t^i \propto w_{t-1}^i p(y_t | x_t^i) \quad (6)$$

As the state vector x operates on multiple (m) joints simultaneously, it eventually preserves the interconnection between body segments. However, it may not be responsible to keep the individual bone length constant. To achieve this and harness the power of particles, in the proposed filtering approach, a population based Genetic algorithm is employed. Even so, this technique has to deal with two objectives i.e., (a) the filtered coordinates should not deviate abruptly from the original coordinates obtained from Kinect® and (b) minimize the bone lengths' variations over time. Mathematically the objective function for each particle i at t is formulated as given below in equation (7) and (8) by way of examples:

$$\max_{x_t} \sum_{j=1}^{2*m} w(j)_t^i \quad (7)$$

$$\min_{x_t} \sum_{\forall valid\, i,j} (l(x_t)_{i,j} - L_{i,j})^2 \quad (8)$$

More particularly, equations (7) and (8) represent a first cost function and a second cost respectively, that are computed and used for the particle filter. In other words, in an embodiment of the present disclosure, at step 204f, the one or more hardware processors 100 compute the first cost function based on the updated weight associated with each of the plurality of particles. This ensures that the dependencies are intact for common joint positions. Similarly, at step 204g, the one or more hardware processors 100 compute the second cost function based on (i) one or more body length segments derived from the plurality of particles and (ii) the one or more actual body length segments.

Figure 4:
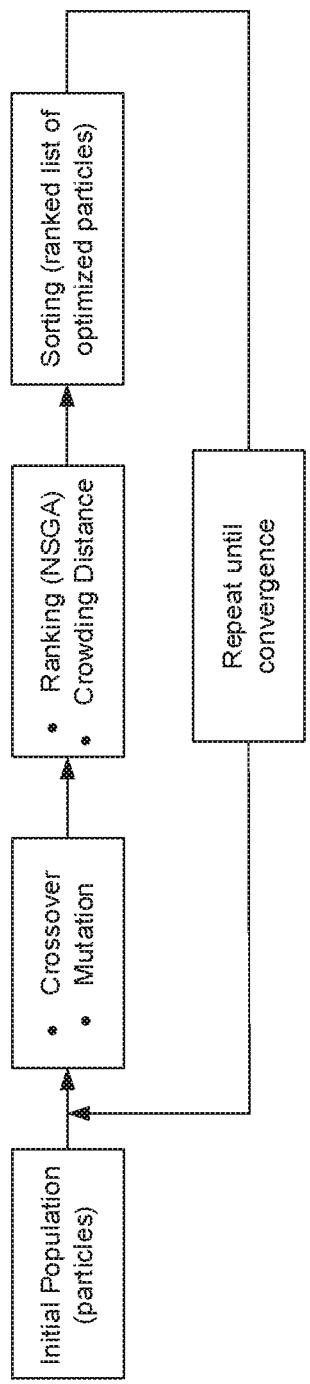
FIG. 4 depicts an exemplary a flow diagram illustrating a method involved in optimization of cost functions (e.g., first cost function and the second cost function) using the system of FIG. 1 in accordance with an embodiment of the present disclosure.

In the above equations (7) and (8), $\{I_{i,j}|(i,j)\leq N$ and $i\neq j\}$ is bone length vector computed from S and $L=\{L_{i,j}|(i,j)\leq N$ and $i\neq j\}$ is the actual lengths (ground truth) of the segments. According to above equation (7) maximizing the sum of weights of all the state variables at a particular time step ensures that the filtered coordinates are close to the measurement vector $y_t$, as w is modeled as likelihood function in above equation (6). This type of multi-objective optimization is handled by NSGA (e.g., refer to S. M. K. Heris and H. Khaloozadeh, "Non-dominated sorting genetic filter a multi-objective evolutionary particle filter," in 2014 Iranian Conference on Intelligent Systems (ICIS), pp. 1-6). S particles form the initial population vector of NSGA and undergo multiple steps as depicted in the FIG. 4 to provide optimized particles. More particularly, FIG. 4, with reference to FIGS. 1 through 3, depict an exemplary a flow diagram illustrating a method involved in optimization of cost functions (e.g., first cost function and the second cost function) using the system 100 of FIG. 1 in accordance with an embodiment of the present disclosure. More particularly, FIG. 4 depicts adjusting value of cost functions (e.g., the first cost function and the second cost function). Specifically, value for optimizing the value of the first cost function and the second cost function ranges between 0 to 1, in one example embodiment. In other words, at step 204h, the one or more hardware processors 104, concurrently optimize, using an optimizing technique, the first cost function and the second cost function to obtain a ranked list of optimized particles based on the plurality of particles. In an embodiment, both the first cost function and the second cost function are optimized in parallel. In an embodiment, the optimizing technique is a Non-dominated Sorting Genetic Technique (NSGT technique) which is also referred as Non-dominated Sorting Genetic Algorithm (NSGA). For instance, in the present disclosure, the first cost function is maximized and the second cost function is minimized to a value that ranges from 0 to 1 until the ranking of optimized particles is achieved.

FIG. 4 is better understood by way of example as below:

NSGA (Non-Dominated Sorting in Genetic Algorithms) is a popular non-domination based genetic algorithm for multi-objective optimization. Population initialization is done based on particles that are generated from output produced by a particle filter technique. Based on non-domination the initialized population is sorted and then crowding distance is assigned. Since individuals are selected based on rank and crowding distance, all the individuals in the sorted population are assigned a crowding distance value. Crowding distance is assigned front wise wherein crowding distance between two individuals is compared in different front which appears to be meaning-less. The basic idea behind the crowing distance is to find Euclidian distance between each individual in a front based on their 'm' objectives in a 'n' dimensional hyper space. The individuals in the boundary are (always) selected since they have infinite distance assignment. Once the individuals are sorted based on non-domination and with crowding distance assigned, the selection is carried out using a crowded comparison-operator. The individuals are selected by using a binary (tournament) selection with the crowed comparison-operator. In crossover phase, two vectors are randomly picked up from a mating pool and some portions of these are exchanged to create two new strings. If a crossover probability of "p" is used, then 100×p % strings are used in the crossover and 100×(1−p) % of the population is used for possible mutation. In Recombination and Selection phase offspring, population is combined with current generation population and selection is performed to set the individuals of the next generation. Elitism is ensured since all previous and current best (optimal) individuals are added in the population wherein population gets sorted based on non-domination. The new generation is filled by each front subsequently until the population size exceeds the current population size (which may be considered as a stopping criteria). Only the best N individuals are selected, where N is the population size wherein selection is based on rank and the on crowding distance on the last front. And hence the process repeats to generate the subsequent generations until an optimized ranked list of particles is finally obtained. The above exemplary description on NSGA can be further understood by way of research studies (e.g., refer to A. Konak, D. W. Coit, A. E. Smith, "Multi-Objective Optimization Using Genetic Algorithms: A Tutorial," CiteSeerX e-prints, 2006) and A. Seshadri, "A Fast and Elitist Multi-Objective Genetic Algorithm: NSGA-II," KanGAL Report No. 200001, 2000, pp. 1-20).

In an embodiment of the present disclosure, at step 204i, the one or more hardware processors 104 adjust the updated weight associated with each of the plurality of particles based on the ranked list of optimized particles to obtain a final state vector comprising a plurality of corrected body joint positions pertaining to the subject. In an embodiment the final state vector comprises weight mean of distribution of the ranked list of optimized particles. In other words, the weighted mean of the particle distribution is taken as the final estimation of the final state vector at time t and it is expressed as $\hat{x}_t = \Sigma_i w_i x_i$. $\hat{x}_t$, which in turn is expected to provide corrected joint coordinates by satisfying both the constraints as mentioned earlier in the above description. In this scenario, the NSGT helps the particle filter to find the multi-objective solutions by being used as an add-on to original particle filter algorithm. It is to be noted that the degeneracy problem of a particle filter, i.e., most of the weights become insignificant, is avoided by re-sampling strategy as mentioned in conventional method(s) (e.g., refer to Arulampalam et al.). All particles and corresponding weights are uniformly randomly initialized at time instance t=0 and recursively estimated for the successive timestamps. The overall technique (or proposed method) is explained in below exemplary pseudo code:

Pseudo code for the proposed method(s) implemented by the present disclosure and its associated embodiments and systems (e.g., system 100):

```
Initialize:
    Random initialization of particles x₀ⁱ and weights
    w₀ⁱ at t = 0 for i = 1,2, ... , S
loop on t:
for each particle i = 1 to S do
    xₜⁱ ← xₜ₋₁ⁱ + uₜ: state Transition
    wₜⁱ ← p(yₜ|xₜⁱ): weight allocation
    C₁(i) = Σⱼ₌₁^(2*m) w(j)ₜⁱ: 1ˢᵗ Cost function
    C₂(i) = Σ(I∀segments(xₜⁱ) − L∀segments)²: 2ⁿᵈ Cost function
end for
xₜ ← NSGA(xₜ, C₁, C₂): maximize(C₁, minimize(C₂)
wₜⁱ ← wₜ₋₁ⁱ * p(yₜ|xₜⁱ), ∀i
wₜ ← wₜ/Σwₜ
if degenerecy in wₜ then
    (xₜ, wₜ) ← resample(xₜ,wₜ)
end if
x̂ₜ = Σᵢwᵢxₜ
if t < T then
    goto loop
else return
end if
```

Below is an exemplary description of how a dataset was created for conduction experimental results by the system 100 by implementing the proposed method:

Dataset Creation:

Twenty six subjects (age: range 24-55 years, weight: 52 kg-97 kg and height: 1.42 m-1.96 m) with no symptoms of neurophysiological or muscular-skeletal disorders, were chosen for the study by the present disclosure. The subjects performed various active Range Of Motion (ROM) exercises, for example, shoulder abduction/adduction or flexion/extension in front of the Kinect® Xbox One sensor (e.g., IR sensing device) placed at a distance of 'x' meter approximately (e.g., in the present disclosure 'x' meter refers to '2 meter'. In the beginning of the exercise, the subjects were to stand in a stationary posture for 30 seconds and then perform the exercise. Dataset comprises of 25 skeleton joint coordinates for both static and dynamic postures.

Figure 5:
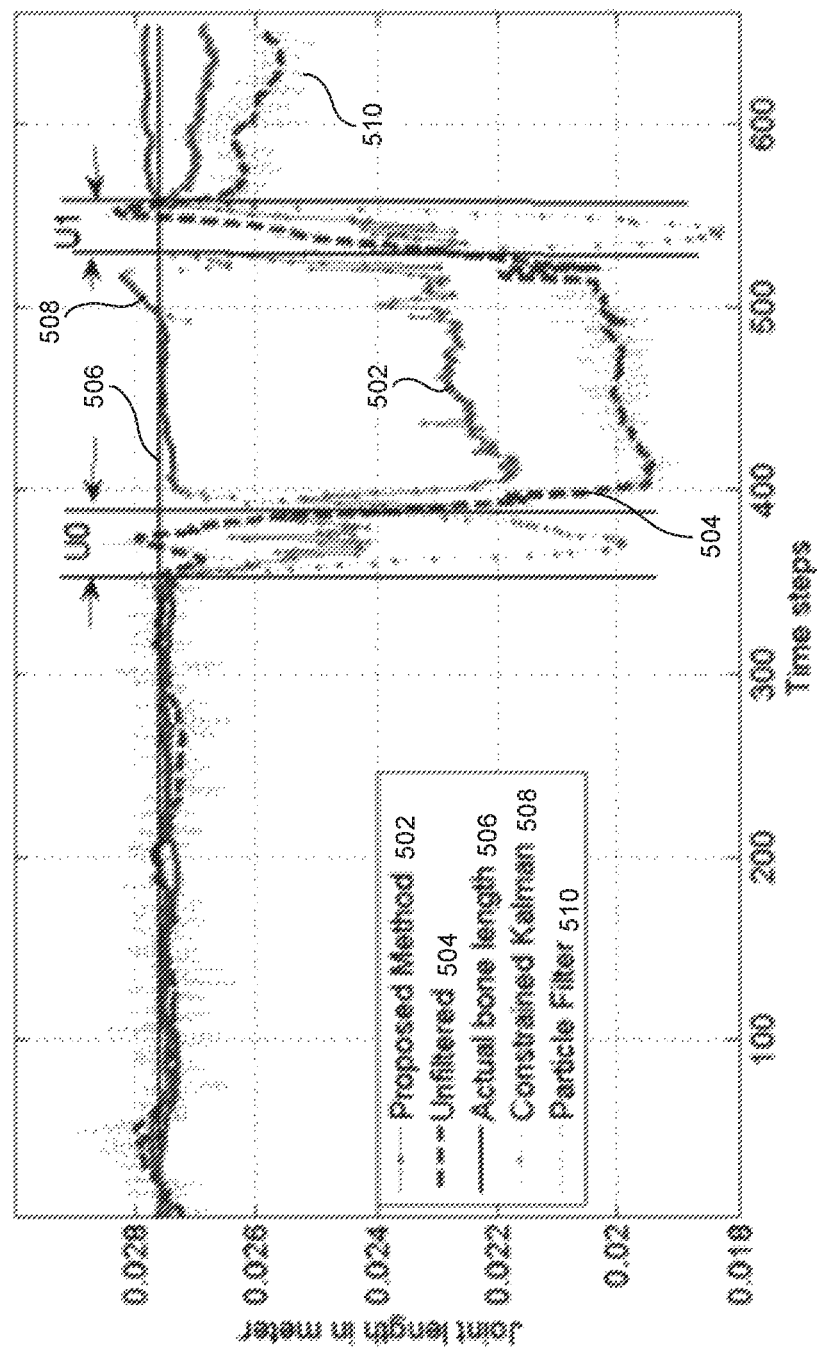
FIG. 5 depicts a graphical representation illustrating variation of right arm length (segment 20-8) of a subject in accordance with an example embodiment of the present disclosure.

Results and Discussions:

The proposed technique (or the above pseudo code) is evaluated on the basis of its ability to minimize the bone lengths' variations computed from the filtered joint coordinates with respect to actual bone lengths. The system 100 and the present disclosure considered joints from both right and left hands simultaneously i.e., 6-5, 5-4, 4-20, 20-8, 8-9, 9-10 as shown in FIG. 3 for filtering. FIG. 5 clearly depicts variation in bone length between joint number 20 and 8 while performing the shoulder abduction/adduction exercise in the right hand (between time steps or frame numbers 380 to 540). More particularly, FIG. 5, with reference to FIGS. 1 through 4, depict a graphical representation illustrating variation of right arm length (segment 20-8) of a subject in accordance with an example embodiment of the present disclosure.

Specifically, in FIG. 5, the dash lines (denoted by 504) clearly depict variation in bone length between joint number 20 and 8 while performing the shoulder abduction/adduction exercise in the right hand (between time steps or frame numbers 380 to 540). Line denoting 506 is representing actual body length segments. Similarly, 508 and 510 represent outputs pertaining to conventional methods (e.g., a constrained Kalman and particle filter, respectively).

Figure 6:
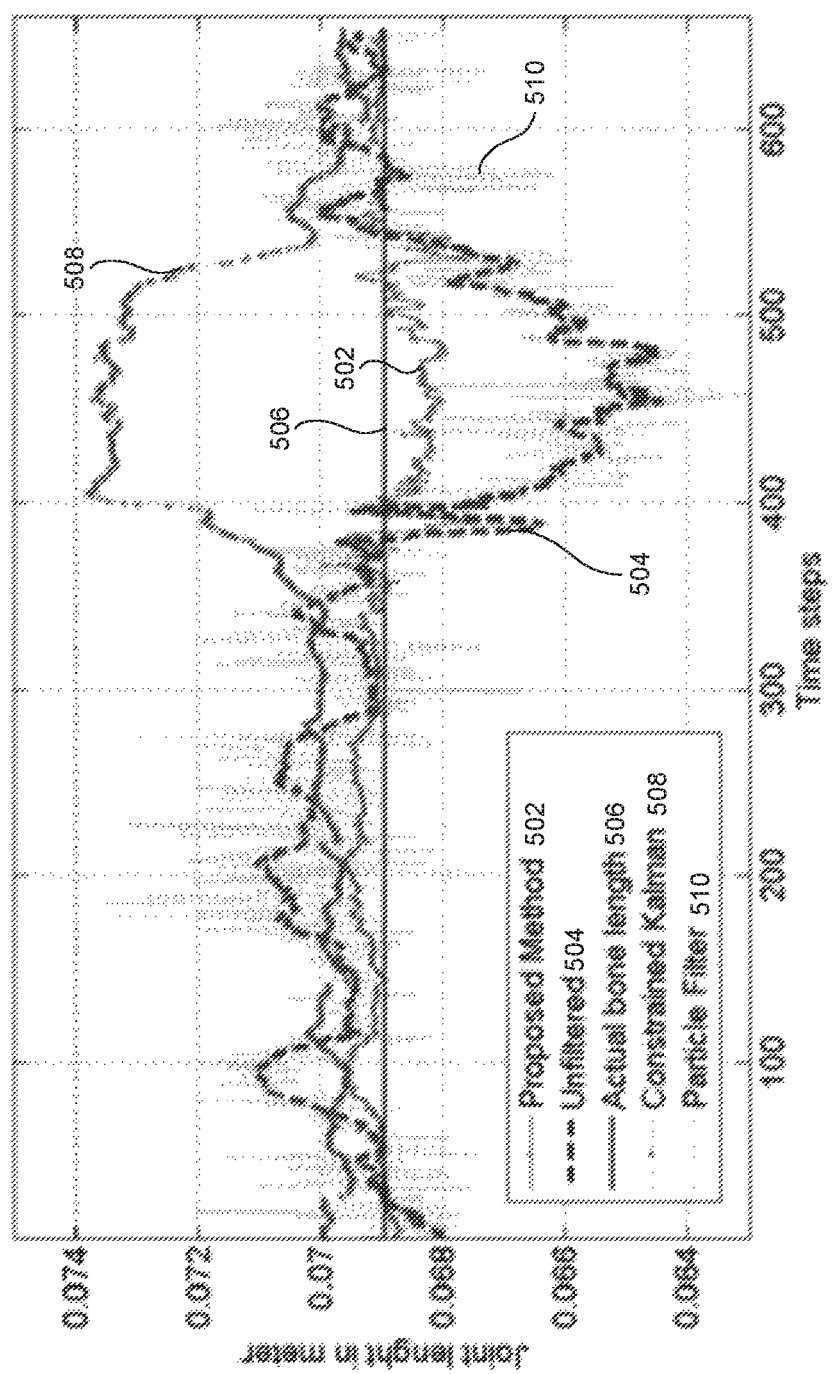
FIG. 6 depicts a graphical representation illustrating variation of left arm length (segment 4-5) of a subject in accordance with an example embodiment of the present disclosure.

Moreover, from FIG. 6 it is quite clear that length of the left arm also varies even it is almost in static posture during the entire exercise. More particularly, FIG. 6, with reference to FIGS. 1 through 5, depict a graphical representation illustrating variation of left arm length (segment 4-5) of a subject in accordance with an example embodiment of the present disclosure. The observation holds true for all other body segment lengths. In order to demonstrate robustness of the proposed technique/method (or pseudo code), it has been applied on the above mentioned seven joints simultaneously and lines (denoted by 502) in FIG. 5 and FIG. 6 portray how it is able to bring the associated segment lengths close to the actual ones. It is quite evident from FIG. 7 that the bone length corrections do not come by randomly (abruptly) adjusting the joint coordinates but by closely following joint positions over time. On the contrary, in conventional method (s) (e.g., refer to Tripathy et al.), the joint coordinates greatly deviates from actual trajectory to satisfy the bone length constraint. Moreover in a very small duration (zone U1 of FIG. 7), the joint coordinate corrected by the convention algorithm described in Tripathy et al. changes drastically which is quite unexpected. More specifically, FIG. 7, with reference to FIGS. 1 through 6, depicts a graphical representation illustrating temporal variation of coordinate "a" for joint number 8 in accordance with an example embodiment of the present disclosure. In FIG. 7, line property 702 depicts and represents output of the proposed method implemented by the system 100 of the present disclosure, line property 704 depicts and represents output of a conventional Kalman filter technique (e.g., refer to Edwards et al.), and line property 706 depicts and represents output of a conventional constrained Kalman technique (e.g., refer to Tripathy et al.). Line 708 depicts and represents output of the unfiltered. Dotted line property 710 depicts and represents output of a conventional particle filter technique (e.g., see Arulampalam et al.). In addition to that, FIGS. 5 and 6 also depict performance comparison of the proposed method with respect to state-of-the-art technique(s) (or conventional algorithms discussed in Tripathy et al. and Arulampalam et al.) for right and left arm lengths. The outcome of a constrained Kalman filter (e.g., Tripathy et al.) appears to be inferior when compared with to the proposed approach for both dynamic (right arm) and static body segments (left arm) because the formulation does not include the interconnection between the joints. In FIGS. 5 through 7, 'x-axis' is represented by time steps and 'y-axis' is represented by coordinates in meters, in one example embodiment.

As shown in FIG. 5, a constrained Kalman filter also fails to adopt the changes in posture as it varies abruptly in zone U1 and U2 (where the right arm starts moving) whereas it performs well in between U1-U2 (where the right arm is at rest). As the formulation of the proposed particle filter (implemented by the system 100) accommodates the inter relationships between body segments, it resists abrupt changes in the bone length and maintains the variation of bone lengths minimum during the transition of body segments from resting state to dynamic state. Moreover, other constraint less methods (e.g., as discussed in Arulampalam et al.) closely follow the unfiltered bone length and performance is not satisfactory compared to the constrained approaches (i.e., Tripathy et al.) and proposed method). The overall performance is evaluated based on the parameter Mean Absolute Percentage Error (MAPE) between the bone length obtained from filtered signal and original signal for all time instances. MAPE (in %) is mathematically defined as in below equation (9). It is desirable to have minimum MAPE to ensure better performance.

$$MAPE = \frac{100}{T}\sum_{t=1}^{T}\left|\frac{L - l(x_t)}{L}\right| \tag{9}$$

Below table (e.g., Table 1) presents the comparison between the proposed method and state-of-the-art algorithms mentioned in conventional research studies (e.g., refer to (i) Tripathy et al.; (ii) Edwards et al.; and Arulampalam et al.).

The evaluation is carried out per bone length based on the average of MAPE over all subjects. Here the constant velocity models are considered for Kalman filter based methods.

TABLE 1

| Segment between joints | Kalman Filter (Edwards et al.) | Constrained Kalman (Tripathy et al.) | Particle Filter (Arulampalam et al.) | Proposed method |
|---|---|---|---|---|
| 20-8 | 15.60 | 13.92 | 17.66 | 3.82 |
| 8-9 | 16.60 | 14.25 | 16.77 | 4.22 |
| 9-10 | 22.01 | 19.57 | 22.52 | 5.69 |

TABLE 1-continued

| Segment between joints | Kalman Filter (Edwards et al.) | Constrained Kalman (Tripathy et al.) | Particle Filter (Arulampalam et al.) | Proposed method |
|---|---|---|---|---|
| 20-4 | 17.17 | 17.17 | 18.39 | 2.71 |
| 4-5 | 13.99 | 13.42 | 14.20 | 1.74 |
| 5-6 | 23.97 | 23.71 | 24.36 | 2.46 |

It is clear and evident from the above Table 1 that the proposed method/technique is able to minimize the MAPE for all segments over all subjects whereas performance of other ones (e.g., conventional research studies) are not so satisfactory. Finally, the proposed particle filter and NSGA based technique outperforms them and is able to achieve a MAPE of 3.44% over all the subjects and all the joints in comparison to a constrained Kalman filter (e.g., Tripathy et al.) with MAPE 17%.

In the present disclosure, a probabilistic framework for estimating the skeleton joint locations using particle filter based joint location estimation approach accompanied with the Non-dominated Sorting Genetic Algorithm has been proposed by the associated embodiments thereof to reduce the variation in bone length. The proposed method by the above observation has enabled to track multiple body segments and can reduce the variation in the segments' length by considering their interconnection in dynamic as well as static conditions. The proposed method and the associated filtering approach is able to preserve the skeleton structure in a more realistic manner. Experimental results on healthy subjects demonstrate remarkable reduction in the MAPE compared to the earlier reported methods including constrained Kalman (e.g., Tripathy et al.) and standalone particle filter (e.g., Arulampalam et al.) approaches.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
   receiving, in a coordinate system, an input data comprising a plurality of body joint positions pertaining to a subject, each of the plurality of body joint positions comprising a plurality of joint coordinates, wherein the plurality of body joint positions are captured by an infrared sensing device; and denoising for each joint, by using a dynamic filtering based technique, the plurality of body joint positions comprising the plurality of joint coordinates to obtain a corrected set of body joint positions pertaining to the subject, wherein the step of denoising the plurality of body joint positions comprises:

computing one or more actual body length segments using a plurality of physically connected joints identified from the plurality of body joint positions;

forming a state vector based on the plurality of physically connected joints identified from the plurality of body joint positions;

tracking at every time instance 't', using the dynamic filtering based technique, a current position of each of the plurality of physically connected joints through an estimation of the formed state vector based on each of the plurality of body joint positions obtained from the input data;

generating a plurality of particles associated with the estimation of the formed state vector;

updating weight of each of the plurality of particles during transition of each of the plurality of particles from one state to another state;

computing a first cost function based on the updated weight associated with each of the plurality of particles;

computing a second cost function based on (i) one or more body length segments derived from the plurality of particles and (ii) the one or more actual body length segments;

concurrently optimizing, using an optimizing technique, the first cost function and the second cost function to obtain a ranked list of optimized particles based on the plurality of particles; and adjusting the updated weight associated with each of the plurality of particles based on the ranked list of optimized particles to obtain a final state vector comprising the corrected set of corrected body joint positions pertaining to the subject.

2. The processor implemented method of claim 1, wherein the optimizing technique is a Non-dominated Sorting Genetic Technique (NSGT).

3. The processor implemented method of claim 1, wherein the dynamic filtering technique comprises a Linear Dynamic System (LDS) filtering technique.

4. The processor implemented method of claim 1, wherein the plurality of particles are generated using an Importance Density Function (IDF).

5. The processor implemented method of claim 1, wherein each of the one or more actual body length segments is computed based on Euclidean distance between two physically connected joints identified from the plurality of body joint positions.

6. The processor implemented method of claim 1, wherein the final state vector comprises weighted mean of distribution of the ranked list of optimized particles.

7. A system comprising:
a memory storing instructions;
one or more communication interfaces; and
one or more hardware processors coupled to the memory via the one or more communication interfaces, wherein the one or more hardware processors are configured by the instructions to:
receive, in the system, an input data comprising a plurality of body joint positions pertaining to a subject, each of the plurality of body joint positions comprising a plurality of joint coordinates, wherein the plurality of body joint positions are captured by an infrared sensing device; and denoise for each joint, by using a dynamic filtering based technique, the plurality of body joint positions comprising the plurality of joint coordinates to obtain a corrected set of body joint positions pertaining to the subject, wherein the plurality of body joint positions are denoised by:

computing one or more actual body length segments using a plurality of physically connected joints identified from the plurality of body joint positions;

forming a state vector based on the plurality of physically connected joints identified from the plurality of body joint positions;

tracking at every time instance 't', using the dynamic filtering based technique, a current position of each of the plurality of physically connected joints through an estimation of the formed state vector based on each of the plurality of body joint positions obtained from the input data;

generating a plurality of particles associated with the estimation of the formed state vector;

updating weight of each of the plurality of particles during transition of each of the plurality of particles from one state to another state;

computing a first cost function based on the updated weight associated with each of the plurality of particles;

computing a second cost function based on (i) one or more body length segments derived from the plurality of particles and (ii) the one or more actual body length segments;

concurrently optimizing, using an optimizing technique, the first cost function and the second cost function to obtain a ranked list of optimized particles based on the plurality of particles; and adjusting the updated weight associated with each of the plurality of particles based on the ranked list of optimized particles to obtain a final state vector comprising the corrected set of body joint positions pertaining to the subject.

8. The system of claim 7, wherein the optimizing technique is a Non-dominated Sorting Genetic Technique (NSGT).

9. The system of claim 7, wherein the dynamic filtering technique comprises a Linear Dynamic System (LDS) filtering technique.

10. The system of claim 7, wherein the plurality of particles are generated using an Importance Density Function (IDF).

11. The system of claim 7, wherein each of the one or more actual body length segments is computed based on Euclidean distance between two physically connected joints identified from the plurality of body joint positions.

12. The system of claim 7, wherein the final state vector comprises weighted mean of distribution of the ranked list of optimized particles.

13. One or more non-transitory machine readable information storage media storing instructions which, when executed by one or more hardware processors, cause the one or more processors to perform a method comprising:
receiving, in a coordinate system, an input data comprising a plurality of body joint positions pertaining to a subject, each of the plurality of body joint positions comprising a plurality of joint coordinates, wherein the plurality of body joint positions are captured by an infrared sensing device; and denoising for each joint, by using a dynamic filtering based technique, the plurality of body joint positions comprising the plurality of joint coordinates to obtain a corrected set of body joint positions pertaining to the subject, wherein the step of denoising the plurality of body joint positions comprises:

computing one or more actual body length segments using a plurality of physically connected joints identified from the plurality of body joint positions; forming a state vector based on the plurality of physically connected joints identified from the plurality of body joint positions;

tracking at every time instance 't', using the dynamic filtering based technique, a current position of each of the plurality of physically connected joints through an estimation of the formed state vector based on each of the plurality of body joint positions obtained from the input data;

generating a plurality of particles associated with the estimation of the formed state vector;

updating weight of each of the plurality of particles during transition of each of the plurality of particles from one state to another state;

computing a first cost function based on the updated weight associated with each of the plurality of particles; computing a second cost function based on (i) one or more body length segments derived from the plurality of particles and (ii) the one or more actual body length segments;

concurrently optimizing, using an optimizing technique, the first cost function and the second cost function to obtain a ranked list of optimized particles based on the plurality of particles; and adjusting the updated weight associated with each of the plurality of particles based on the ranked list of optimized particles to obtain a final state vector comprising the corrected set of corrected body joint positions pertaining to the subject.

14. The one or more non-transitory machine readable information storage media of claim 13, wherein the optimizing technique is a Non-dominated Sorting Genetic Technique (NSGT).

15. The one or more non-transitory machine readable information storage media of claim 13, wherein the dynamic filtering technique comprises a Linear Dynamic System (LDS) filtering technique.

16. The one or more non-transitory machine readable information storage media of claim 13, wherein the plurality of particles are generated using an Importance Density Function (IDF).

17. The one or more non-transitory machine readable information storage media of claim 13, wherein each of the one or more actual body length segments is computed based on Euclidean distance between two physically connected joints identified from the plurality of body joint positions.

18. The one or more non-transitory machine readable information storage media of claim 13, wherein the final state vector comprises weighted mean of distribution of the ranked list of optimized particles.

* * * * *